(12) United States Patent
Hoang et al.

(10) Patent No.: US 6,371,675 B1
(45) Date of Patent: Apr. 16, 2002

(54) SKIN DISINFECTANT APPLICATOR

(75) Inventors: Minh Q. Hoang, Taylorsville; Jonathan K. Burkholz, Salt Lake City, both of UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/741,562

(22) Filed: Dec. 20, 2000

(51) Int. Cl.[7] ............................................. A61M 35/00
(52) U.S. Cl. ...................... 401/205; 401/264; 401/135; 604/3
(58) Field of Search ................................ 401/205, 206, 401/135, 264; 604/1–3

(56) References Cited

U.S. PATENT DOCUMENTS

| | | | |
|---|---|---|---|
| 3,108,314 A | 10/1963 | House ........................ 15/566 |
| 3,231,145 A | * 1/1966 | Converse .................... 401/264 |
| 3,384,438 A | * 5/1968 | Sherbondy .................. 401/264 |
| 3,617,139 A | 11/1971 | Ross .......................... 401/206 |
| 3,757,782 A | 9/1973 | Aiken ........................ 128/269 |
| 4,053,243 A | 10/1977 | Levin ......................... 401/186 |
| 4,183,684 A | 1/1980 | Avery, Jr. ................... 401/133 |
| 4,201,491 A | * 5/1980 | Kohler ....................... 401/206 |
| 4,620,648 A | * 11/1986 | Schwartzman .............. 401/206 |
| 4,652,163 A | 3/1987 | Karliner et al. ............. 401/195 |
| 4,747,720 A | 5/1988 | Bellehumeur et al. ...... 401/205 |
| 4,925,327 A | 5/1990 | Wirt ........................... 401/205 |
| 4,957,385 A | 9/1990 | Weinstein ................... 401/132 |
| 5,308,180 A | 5/1994 | Pournoor et al. ........... 401/205 |
| 5,435,660 A | 7/1995 | Wirt ........................... 401/135 |
| 5,538,353 A | 7/1996 | DeHavilland ............... 401/132 |
| 5,658,084 A | 8/1997 | Wirt ........................... 401/132 |
| 5,690,958 A | 11/1997 | McGrath .................... 424/451 |
| 5,713,843 A | 2/1998 | Vangsness .................... 604/3 |
| 5,791,801 A | 8/1998 | Miller ........................ 401/132 |
| 5,916,882 A | 6/1999 | Jeng ........................... 514/57 |
| 5,931,590 A | 8/1999 | Harris .......................... 401/6 |
| 5,934,296 A | 8/1999 | Clay .......................... 132/320 |

FOREIGN PATENT DOCUMENTS

| | | | | |
|---|---|---|---|---|
| FR | 2 722 695 A1 | 7/1994 | ......... | A61M/35/00 |
| WO | WO 99/63934 | 12/1999 | | |

* cited by examiner

Primary Examiner—Charles R. Eloshway
(74) Attorney, Agent, or Firm—Eric M. Lee

(57) ABSTRACT

The applicator for an anti-microbial prep solution of this invention includes a generally hollow handle having a closed proximal end and an open distal end, a foam pad attached to the hollow handle over the open distal end, and a slit formed in the foam pad that acts as a flow control valve.

4 Claims, 10 Drawing Sheets

SKIN DISINFECTANT APPLICATOR

BACKGROUND OF THE INVENTION

This invention relates to an applicator that can be used by a healthcare professional to apply an anti-microbial solution, such as an alcohol-based prep solution, to a patient's skin. Such an alcohol-based prep solution can be used for IV and surgical site preparation and as a general skin disinfectant.

Because microorganisms lie on the skin, standard invasive medical procedures require the patient's skin where the procedure is to take place to be disinfected prior to the procedure. This skin preparation is important in order to minimize the risk of infection to the patient.

Alcohol has long been recognized as a fast acting broadspectrum disinfectant. Alcohol-based prep solutions have many advantages over soap or water based prep solutions, such as reduced prepping and solution drying time. However, alcohol is flammable and its use and application on a patient must be carefully controlled in order to minimize the fire hazard created when such an alcohol-based prep solution is used. Indeed, in its January 1992 Guidance on Surgical Fires, the ECRI stated that approximately ten surgical patient fires come to its attention per year. Most of these fires ignite on or in the patient and obviously can cause considerable injury to the patient. The ECRI estimate that this problem is more severe than the numbers would indicate because it believes that numerous other unreported fires occur. This problem is exacerbated today since today's surgical suites and other patient care facilities include a significant number of electrical equipment that may come in contact with the patient. For example, such electrical equipment includes patient monitoring devices, electrosurgical or electrocautery devices, defibrillators, heated probes, drills, burs, argon beam coagulators, fiberoptic light sources and cables and lasers, which all may be used on and around the patient. In addition, the atmosphere in surgical suites and other patient care facilities is made more combustible because of the common use of oxygen there.

Many different anti-microbial applicators exist but could be improved. Some applicators allow the anti-microbial solution to flow therefrom in large uncontrolled amounts. Other applicators do not have a mechanism to shut off the flow of the anti-microbial solution once the flow starts so that all of the anti-microbial solution must be dispensed from the applicator. Both of these types of applicators are problematic because they may allow excessive amounts of the anti-microbial solution to flow onto the patient where it could pool and create a significant fire hazard if the anti-microbial solution is flammable. In addition, a patient is often covered by a surgical cloth drape after prepping, i.e. the disinfecting procedure, takes place. Where a significant amount of the anti-microbial solution is placed on a patient, the surgical drape can collect the vapors from the anti-microbial solution as the excess anti-microbial solution vaporizes. Again, if the anti-microbial solution is flammable a potential exists for a severe accident to the patient and the healthcare professionals in the area. Also, this inability to adequately control the flow of anti-microbial solution on and around the patient increases the likelihood that the solution will stain material in the area.

SUMMARY OF THE INVENTION

It is therefore an object of the invention to provide an applicator for an anti-microbial solution that controls the amount of the solution that flows from the applicator.

It is another object of this invention to provide an applicator for an anti-microbial solution that allows the user to stop the flow of the solution therefrom when desired.

It is yet another object of this invention to provide an applicator for an anti-microbial solution that allows the solution to remain in the applicator after some of the solution has been dispensed for subsequent use or disposal.

The applicator for an anti-microbial solution of this invention includes a generally hollow handle having a closed proximal end and an open distal end, a foam pad attached to the hollow handle over the open distal end, and a flow control valve associated with the foam pad. The hollow handle contains the anti-microbial solution therein. Alternatively, the hollow handle may contain an ampoule the holds the anti-microbial solution therein. The flow control valve controls the flow of the anti-microbial solution from the applicator handle to the foam pad and then to the patient. The flow control valve is a slit formed in the foam pad. The slit is designed so that it remains closed when no pressure is exerted on the distal surface of the foam pad. However, when pressure is exerted on the distal surface of the foam pad, such as when the applicator is pressed against a patient's skin, the slit opens to allow the anti-microbial solution to flow past the slit into the foam pad. There the anti-microbial solution can be easily distributed over the patient's skin by the foam pad. When a sufficient amount of the anti-microbial solution has flowed into the foam pad, the healthcare professional can release the pressure exerted on the distal surface of the foam pad to stop the flow of anti-microbial solution out of the applicator handle.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
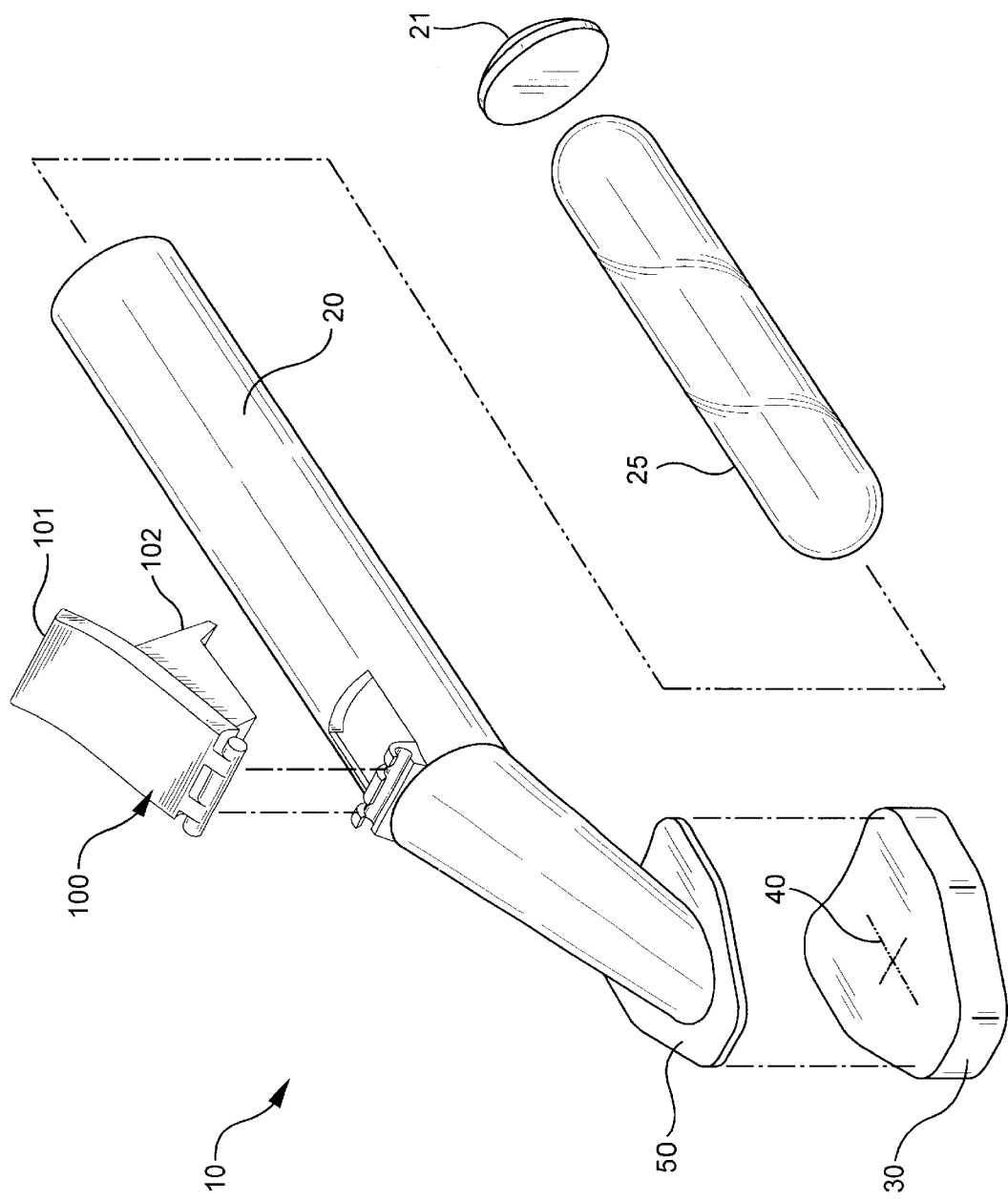
FIG. 1 is an exploded perspective view of the applicator of this invention.
Figure 2:
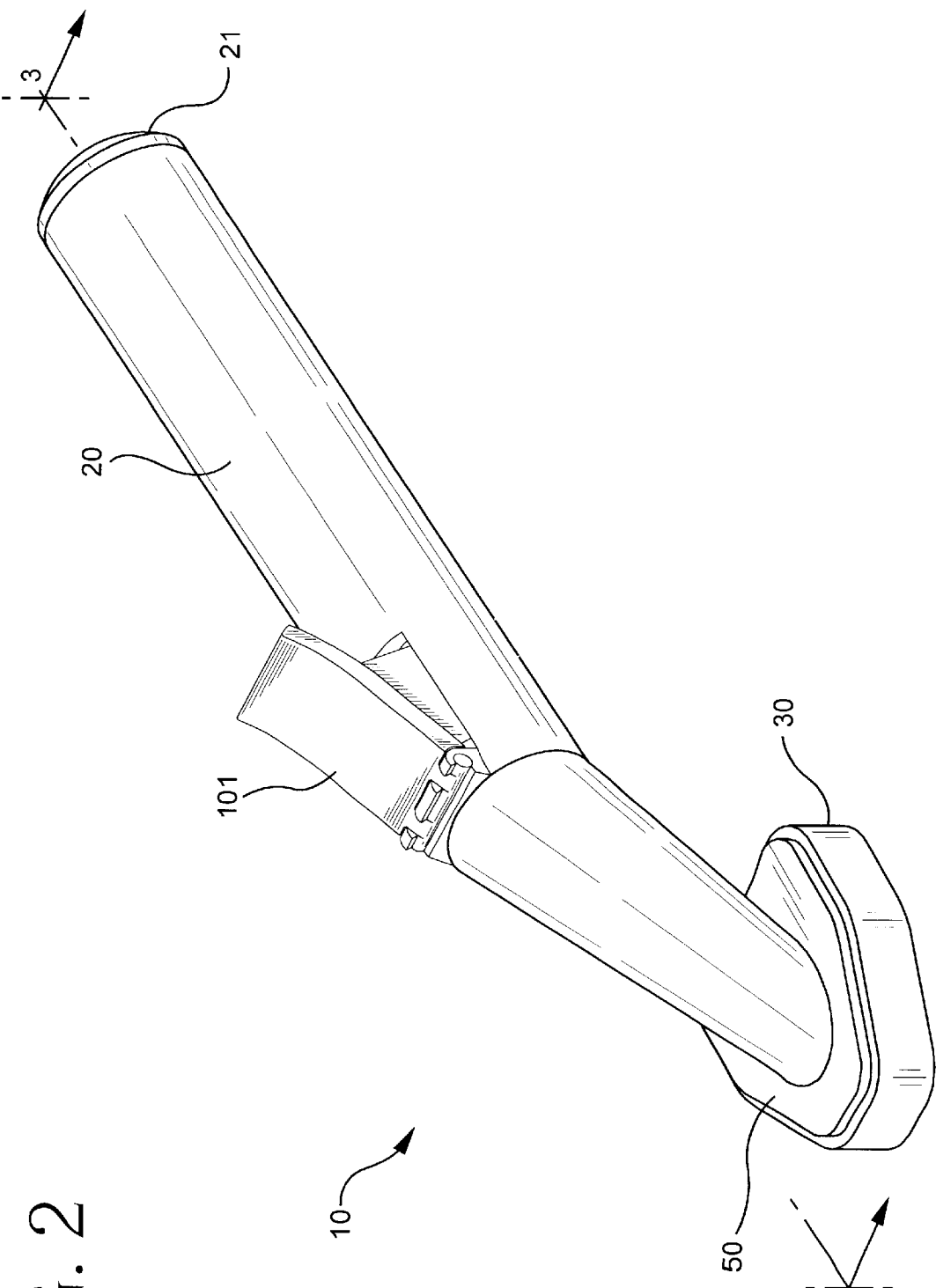
FIG. 2 is a perspective view of the applicator of this invention.
Figure 3:
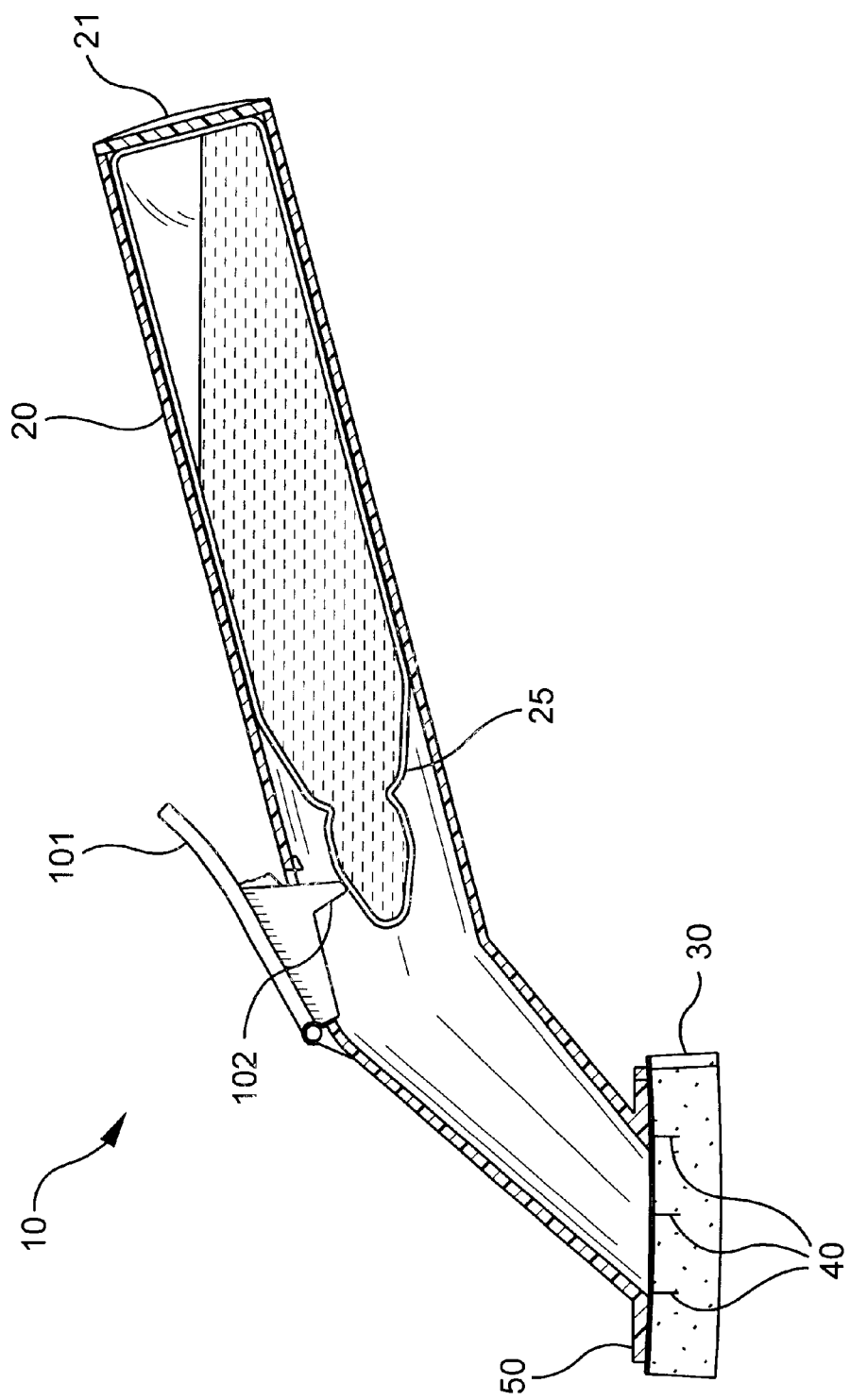
FIG. 3 is a side elevation view in cross section of the applicator of this invention taken along line 3—3 of FIG. 2 prior to the release of the anti-microbial solution from the ampoule contained in the applicator.
Figure 4:
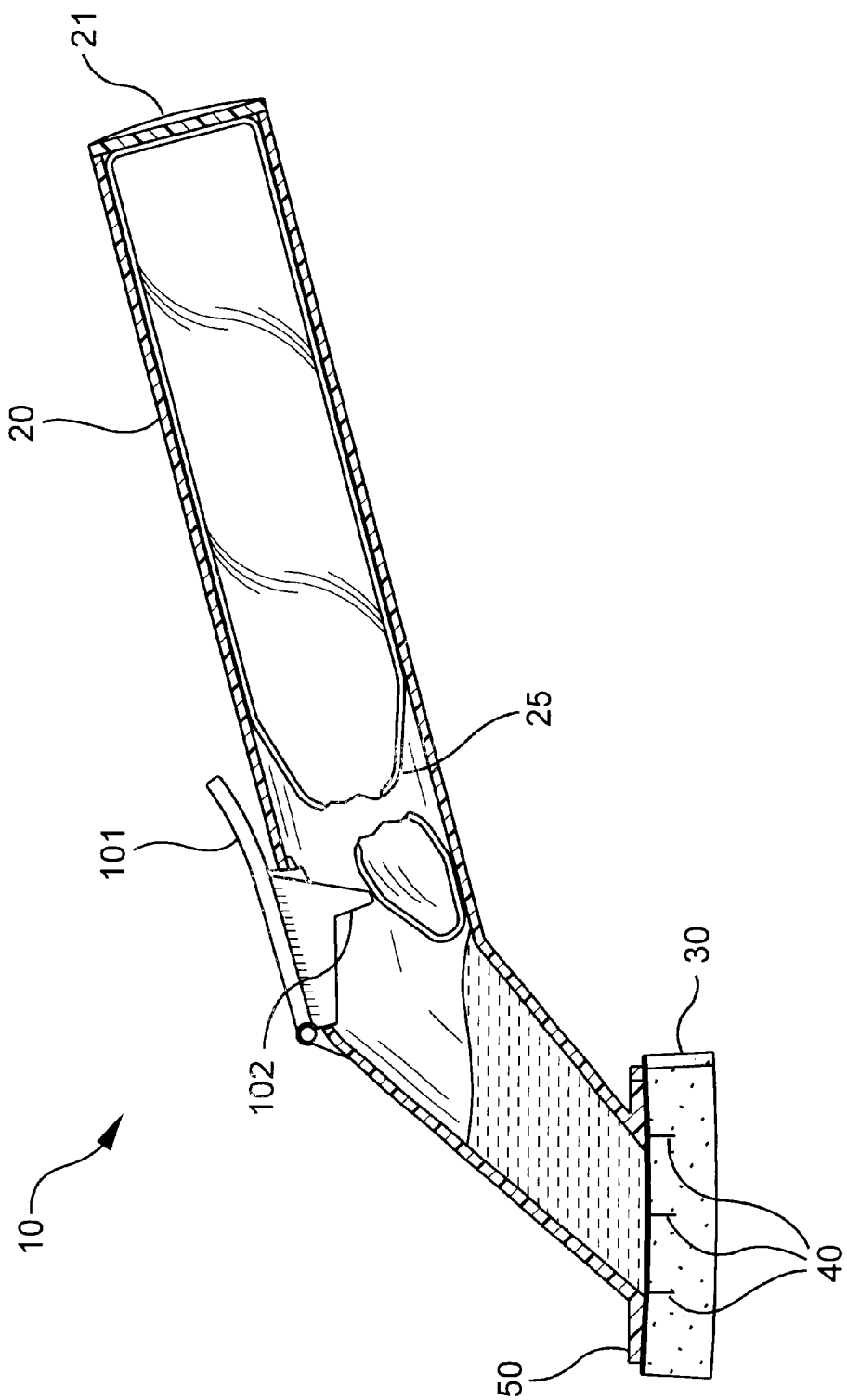
FIG. 4 is a side elevation view in cross section of the applicator of this invention similar to FIG. 3 but after the release of the anti-microbial solution from the ampoule contained in the applicator.
Figure 5:
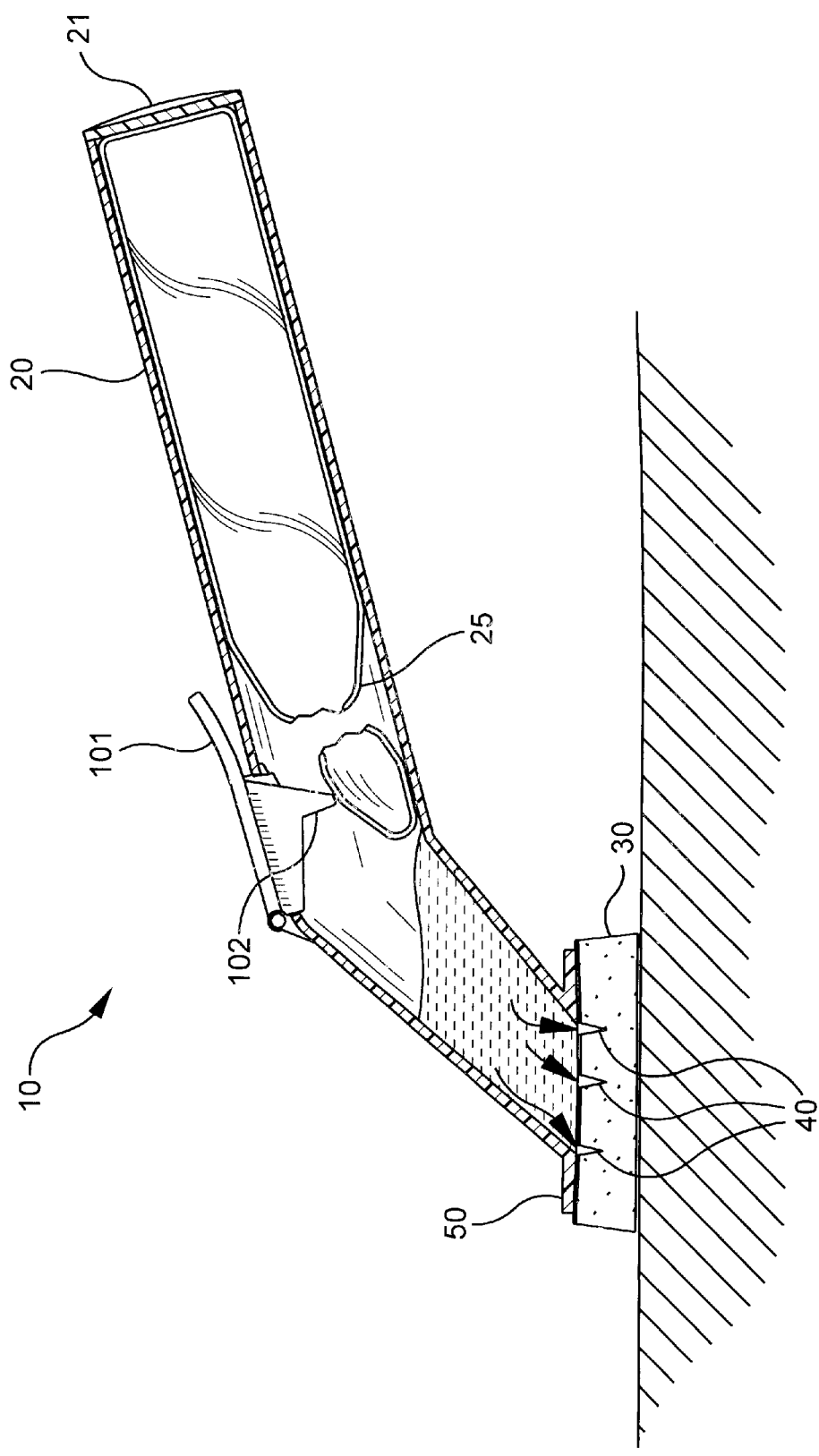
FIG. 5 is a side elevation view in cross section of the applicator of this invention similar to FIG. 4 but showing the applicator being pressed on a surface such as a patient's skin.
Figure 8:
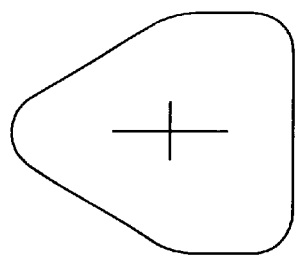
FIGS. 7–33 are top plan views of various geometric shapes that may be used for the face of the foam pad used on the applicator of this invention and various slit patterns that may be used for the foam pad used on the applicator of this invention.
Figure 11:
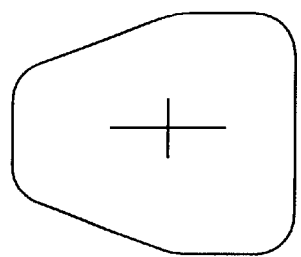
Figure 7:
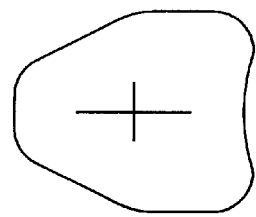
Figure 10:
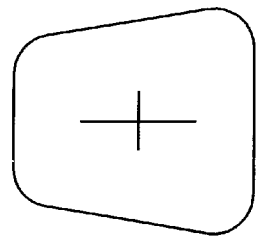
Figure 6:
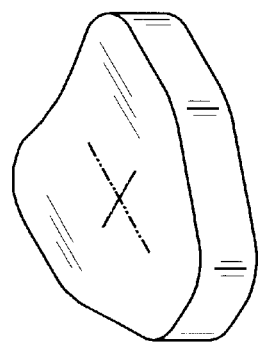
FIG. 6 is a perspective view of a geometric shape that may be used for the foam pad used on the applicator of this invention.
Figure 9:
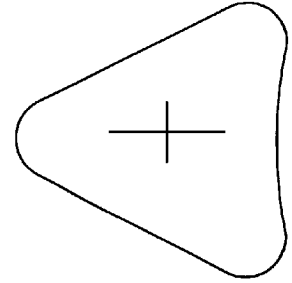
Figure 12:
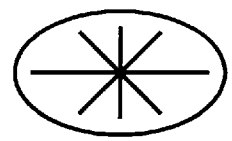
Figure 13:
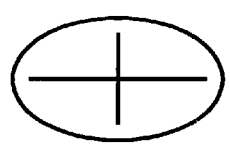
Figure 14:
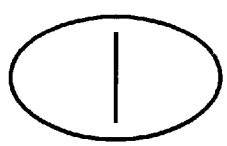
Figure 15:
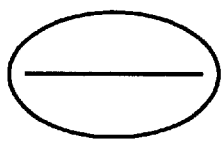
Figure 16:
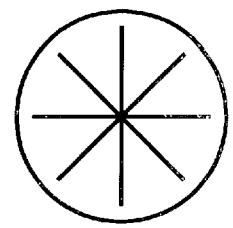
Figure 17:
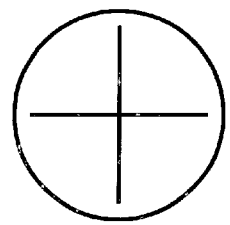
Figure 18:
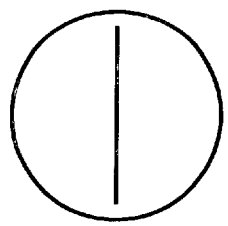
Figure 19:
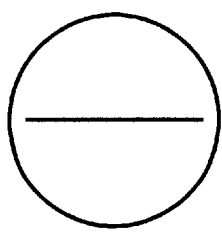
Figure 20:
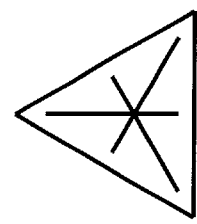
Figure 21:
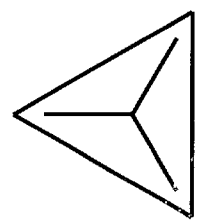
Figure 22:
Figure 23:
Figure 24:
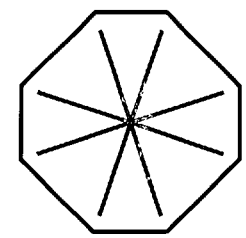
Figure 25:
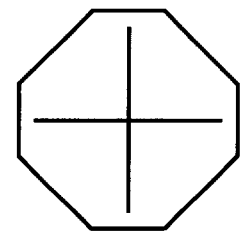
Figure 26:
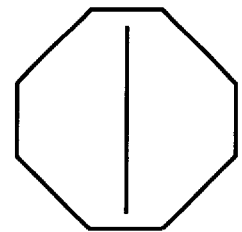
Figure 27:
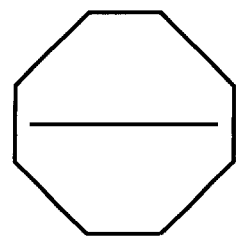
Figure 28:
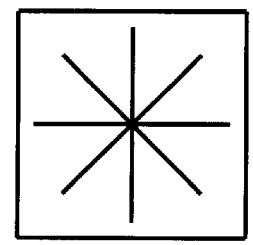
Figure 29:
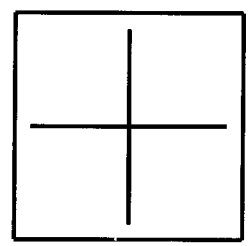
Figure 30:
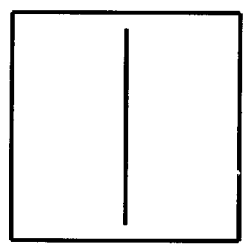
Figure 31:
Figure 32:
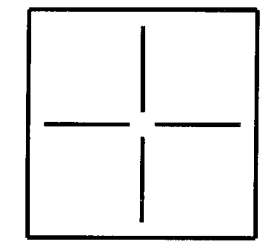
Figure 33:
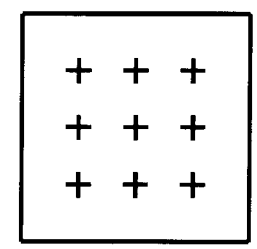

As used herein, the term "proximal" refers to a location on the applicator for an anti-microbial solution of this invention that, during normal use, is closest to the clinician using the device and farthest from the patient in connection with whom the device is used. Conversely, the term "distal" refers to a location on the applicator of this invention that, during normal use, is farthest from the clinician using the device and closest to the patient in connection with whom the device is used.

As used herein, the term "top", "up" or "upwardly" refers to a location on the applicator for an anti-microbial solution of this invention that, during normal use, is radially away from the device and away from the patient's skin. Conversely, as used herein, the term "bottom", "down" or "downwardly" refers to a location on the applicator of this invention that, during normal use, is radially away from the device and toward the patient's skin.

As used herein, the term "in" or "inwardly" refers to a location with respect to the applicator for an anti-microbial solution of this invention that, during normal use, is toward the inside of the device. Conversely, as used herein, the term "out" or "outwardly" refers to a location with respect to the applicator of this invention that, during normal use, is toward the outside of the device.

Although the applicator of this invention is described for use with an alcohol-based anti-microbial prep solution, it is to be understood that any liquid anti-microbial prep solution may be used with the applicator.

The applicator 10 for an anti-microbial solution of this invention includes a generally hollow handle 20 having a closed proximal end and an open distal end, and a foam pad 30 attached to hollow handle 20 over the open distal end. Hollow handle 20 contains the anti-microbial solution therein. Alternatively, hollow handle 20 may contain an ampoule 25 that holds the anti-microbial solution therein. Foam pad 30 is formed with a slit 40 therein that acts as a flow control valve to control the flow of the anti-microbial solution from hollow handle 20 to foam pad 30 and then to the patient. Slit 40 is designed so that it remains closed when no pressure is exerted on the distal surface of foam pad 30. However, when pressure is exerted on the distal surface of foam pad 30, such as when applicator 10 is pressed against a patient's skin, slit 40 opens to allow the anti-microbial solution to flow past slit 40 into foam pad 30. There the anti-microbial solution can be easily distributed over the patient's skin by foam pad 30. When a sufficient amount of the anti-microbial solution has flowed into foam pad 30, the clinician can release the pressure exerted on the distal surface of foam pad 30 to stop the flow of anti-microbial solution out of hollow handle 20.

Hollow handle 20 can take any configuration desired. However, preferably it has a generally tubular, dog-leg configuration where the angle is about 15 degrees, although an angle of up to about 30 degrees is acceptable. Hollow handle 20 may be over-molded with a soft material, such as polyisoprene or the like, that is easily gripped and more comfortable to the clinician. Preferably, hollow handle 20 is formed from a transparent or translucent polymer, such as low, medium or high density polyethylene, PET or the like. Since most prep solutions are colored with a dye or naturally are brown, such as iodine, this feature will allow the clinician to easily determine the amount of anti-microbial solution remaining in hollow handle 20.

The open proximal end of hollow handle 20 is sealed with a plug 21 that may be press fit or screw fit therein. A port may be formed in plug 21 to allow air to flow into hollow handle 20 as the anti-microbial solution flows out of hollow handle 20. If ampoule 25 is used, it is preferably located in the proximal portion of hollow handle 20. In such a case, a means for opening the ampoule is associated with hollow handle 20. Such a means is shown in the FIGS. as a lever 100 with an arm 101 and a pressure finger 102 extending therefrom. Pressure finger 102 is designed to break off a frangible portion of ampoule 25 to release the anti-microbial solution therefrom. See our co-pending patent application, U.S. application Ser. No. 09/741,516 for a variety of other means for breaking ampoule 25.

Foam pad 30 is attached to hollow handle 20 over its open distal end by adhesive, flame bonding or any other suitable means. Preferably, the longitudinal axis of foam pad 30 is oriented at about 45 degrees to the longitudinal axis of the distal portion of hollow handle 20 although an angle between about 30 degrees and about 60 degrees is acceptable. Foam pad 30 is comprised of two or more layers of laminated material. The top layer is preferably a substantially non-porous, hydrophobic material such as polyethylene, polypropylene, silicone, or other plastic material. Such a material substantially limits the flow of anti-microbial solution into the bottom layer. Preferably, the bottom layer is an open cell foam, such as polyurethane or other suitable open cell foam material, that allows the anti-microbial solution to pass therethrough. Alternatively, foam pad 30 can be formed from a single layer of foam. In such a case, the top portion of foam pad 30 preferably is less porous (more dense) than the bottom portion of foam pad 30. The varying porosity can be achieved by a number of different techniques. For example, the top portion of foam pad 30 can be flame treated or a thin layer of adhesive can be applied over the top portion of foam pad 30. In addition, foam pad 30 can be curved so the center of the radius of curvature is located proximally of the top portion of foam pad 30. This arrangement restricts or closes the open cell structure along the top portion of foam pad 30. With any of the foregoing techniques, the flow of anti-microbial solution from hollow handle 20 into the bottom portion of foam pad 30 is reduced.

The face of foam pad 30 can have any shape desired. See FIGS. 6 through 33. It can have a generally square or rectangular shape, a trapezoidal shape, a shape analogous to home plate in baseball, a circular shape, an elliptical shape or a triangular shape. The foregoing examples are illustrative only and in no way limit the invention.

A single slit may be used or a plurality of slits formed in top layer 31 in any pattern desired may be used to act as a flow control valve. See FIGS. 6 through 33. Where one slit is used, it is preferably aligned on an axis of the face of foam pad 30. If a plurality of slits is used, the slits can radiate out in any direction from the center of the face of foam pad 30. The slits do not have to be straight but could be angled, curved or undulating. Alternatively, the plurality of slits could be formed as a plurality of short single or crossed lines aligned or randomly placed on the face of foam pad 30. The particular pattern of slits that is used, as well as the foam density, the slit depth and the geometry of the open distal end of hollow handle 20, will affect the rate of flow of the anti-microbial solution. Again, the foregoing examples for the slit pattern are illustrative only and in no way limit the invention.

Figure 35:
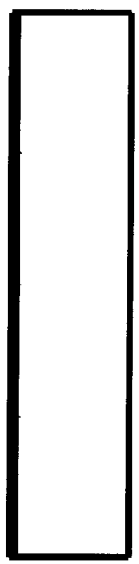
FIG. 35 is a side elevation view in cross section of the foam pad used on the applicator of this invention showing a first depth of penetration of the slits.
Figure 36:
FIG. 36 is a side elevation view in cross section of the foam pad used on the applicator of this invention showing a second depth of penetration of the slits.
Figure 37:
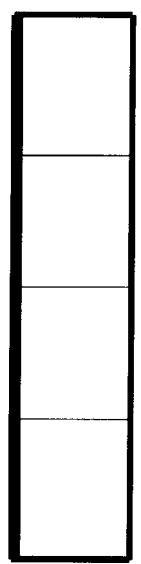
FIG. 37 is a side elevation view in cross section of the foam pad used on the applicator of this invention showing a third depth of penetration of the slits.

Slit 40 can extend through only the top layer or the top portion of foam pad 30. See FIG. 35. Alternatively, slit 40 can extend to about the middle of foam pad 30 so slit 40 passes through top layer or the top portion of foam pad 30 and a portion of the bottom layer or the bottom portion of foam pad 30. See FIG. 36. In addition, slit 40 can extend entirely through foam pad 30. See FIG. 37. Where a plurality of slits are used, the depth of penetration of each slit could vary. The depth of penetration will affect the rate of flow of the anti-microbial solution. The slit penetration depth should be approximately to the middle of the foam pad. This depth ensures that there is adequate flow of the solution while assuring that slit 40 do not open prior to and after use. If the slit penetration depth is too shallow, slit 40 may not open up sufficiently to permit an adequate amount of solution flow. Alternatively, if the slit penetration depth is too great, the distal side of foam pad 30 may not close appropriately upon removal of pressure on the patient's skin. Again, the foregoing examples are illustrative only and in no way limit the invention.

Figure 34:
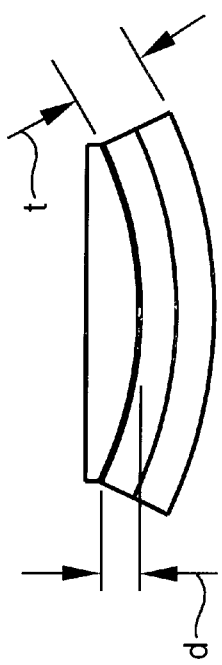
FIG. 34 is a side elevation view in cross section of the foam pad used on the applicator of this invention showing the curvature of the foam pad.

As discussed above, slit 40 remains closed as long as foam pad 30 of applicator 10 is not pressed onto some surface, such as a patient's skin. In order to ensure that slit 40 remains closed under these circumstances, foam pad 30 is preferably curved so the center of the radius of curvature is proximal of foam pad 30. Preferably this curvature is such that the ends of foam pad 30 are offset a particular distance d from the middle of foam pad 30. See FIG. 34. This offset distance can be correlated to the thickness of foam pad 30. Preferably the curvature of foam pad 30 is such that the offset distance is between t/6 and t/4 where t is the thickness of the foam pad. Forming interface 50 with the desired curvature and then adhering foam pad 30 to interface 50 facilitates the provision of the appropriate curvature to foam pad 30.

Once foam pad 30 is pressed onto a patient's skin, slit 40 opens allowing anti-microbial solution to flow into the open cells of foam pad 30. Thereafter, the anti-microbial solution can be dispersed in a controlled manner over the desired patient skin surface area. The curvature of foam pad 30 also increases patient comfort. This is because foam pad 30 will move more smoothly over an uneven surface since there is a reduced likelihood that an edge of foam pad 30 will catch on the patient's skin.

Thus it is seen that an applicator for an anti-microbial prep solution is provided that controls the amount of the solution that flows from the applicator, that allows the user to stop the flow of the solution therefrom when desired and that allows the solution to remain in the applicator after some of the solution has been dispensed for subsequent use or disposal.

We claim:

1. An applicator, comprising:

a handle having a closed proximal end and an open distal end;

a foam pad having a substantially non-porous, hydrophobic top portion and a bottom portion together defining a thickness and an end portion and a center portion and being disposed across the open distal end and defining at least one slit extending into the top portion and wherein the foam pad has a radius of curvature that is proximal of the foam pad such that the center portion is offset from the end portion a distance having a value between the thickness divided by six and the thickness divided by four.

2. The applicator of claim 1 wherein the slit extends into the bottom portion.

3. The applicator of claim 1 wherein a plurality of slits extends into the top portion of the foam pad.

4. The applicator of claim 3 wherein the plurality of the slits radiate out from the center portion of the foam pad.

* * * * *